United States Patent [19]

Martins et al.

[11] Patent Number: 4,774,345

[45] Date of Patent: Sep. 27, 1988

[54] AMINE-COMPLEXED ZINC SALTS OF ORGANIC DIACIDS

[75] Inventors: Evon Martins, Somerville; Richard A. Slepetys, Bricktown, both of N.J.

[73] Assignee: Engelhard Corporation, Menlo Park, N.J.

[21] Appl. No.: 882,056

[22] Filed: Jul. 3, 1986

Related U.S. Application Data

[62] Division of Ser. No. 714,709, Mar. 21, 1985.

[51] Int. Cl.⁴ ............................................. C07F 3/06
[52] U.S. Cl. .................................... 556/132; 556/135
[58] Field of Search ................................. 556/132, 135

[56] References Cited

U.S. PATENT DOCUMENTS

| | | | |
|---|---|---|---|
| 2,689,828 | 6/1952 | Smith et al. | 252/34 |
| 2,769,731 | 11/1956 | Schneid et al. | 556/132 X |
| 2,816,051 | 12/1957 | Harford | 148/6.2 |
| 3,046,289 | 7/1962 | Clark | 556/135 |
| 3,058,948 | 10/1962 | Mosimann et al. | 556/135 X |
| 3,163,603 | 11/1964 | LeSuer | 252/33.6 |
| 3,306,908 | 2/1967 | LeSuer | 260/326.3 |
| 3,426,024 | 2/1969 | Harvey | 556/135 X |
| 3,493,508 | 2/1970 | Andress | 556/135 X |
| 3,544,609 | 12/1970 | Forbes et al. | 556/132 |
| 3,551,466 | 12/1970 | Gee et al. | 260/429 |
| 3,557,171 | 1/1971 | Andress | 260/429.9 |
| 3,869,484 | 3/1975 | Burke | 556/132 X |
| 3,876,574 | 4/1975 | Nagahisa et al. | 260/22 |
| 4,011,167 | 3/1977 | Chibnik et al. | 556/135 X |
| 4,191,670 | 3/1980 | Strauch et al. | 260/23 |
| 4,212,674 | 7/1980 | Strauch | 106/14.05 |
| 4,217,142 | 8/1980 | Mayne et al. | 106/14.36 |
| 4,243,417 | 1/1981 | Grourke et al. | 106/14.13 |
| 4,246,030 | 1/1981 | Lipinski | 106/14.12 |
| 4,492,600 | 1/1985 | Brunn et al. | 106/14.34 |

OTHER PUBLICATIONS

Noltes et al, The Journal of Organometallic Chemistry, 3 (1965), pp. 222–228.

*Primary Examiner*—Paul F. Shaver
*Attorney, Agent, or Firm*—Inez L. Moselle

[57] ABSTRACT

Amine-complexed zinc salts of organic diacids selected from the group consisting of (i) dicarboxylic acids, (ii) diphenols, and (iii) phthalic acids. Specifically disclosed compounds include $C_2$–$C_3$ alkylene diamine-complexed zinc salts of thiodiphenol and sulfonyldiphenol, and ethylene diamine-complexed salts of phthalic, isophthalic and terephthalic acids. Such amine-complexed zinc salts have utility as corrosion inhibitors in coating compositions for metallic substrates, e.g., paints based on alkyds, latexes or linseed oil. Also disclosed are anti-corrosion additives, comprising the aforementioned amine-complexed salts distended on mineral fillers such as kaolin, and a method of making same by reaction of zinc oxide, amine, and organic diacid, at elevated temperatures, in an aqueous slurry of the mineral filler. At least the dicarboxylic acid and diphenol derived salts also display utility as inhibitors of marine growth (algae and barnacles) on substrates.

17 Claims, 4 Drawing Sheets

AMINE-COMPLEXED ZINC SALTS OF ORGANIC DIACIDS

This is a divisional application of co-pending application Ser. No. 714,709 filed on Mar. 21, 1985.

BACKGROUND OF THE INVENTION

1. Field of The Invention

The present invention relates to amine-complexed zinc salts of organic diacids, more particularly to amine-complexed zinc salts of dicarboxylic acids, diphenols, and phthalic acids, and to film-forming compositions containing such salts as corrosion inhibitors, for protection of metallic substrates susceptible to corrosion.

2. Description of The Prior Art

In the practice of corrosion control, as applied to ferrous and other metallic substrates susceptible to corrosion, e.g., iron, steel, copper, magnesium, aluminum and alloys thereof, a great number of metallic substrate treatment processes, such as passivation and phosphatizing, and anticorrosion coatings for such metallic substrates, have been developed and employed.

In particular, a large number of protective coatings for metallic substrates susceptible to corrosion have been disclosed and utilized in the prior art. Among such coatings formulations are various inorganic zinc silicate-containing compositions, in which zinc is employed as a pigment and filler in the inorganic silicate binder matrix. Such compositions have utility for coating of ferrous substrates, on which the zinc in the protective coating is galvanically sacrificed to reduce or inhibit corrosion of the underlying metallic substrate. Similarly, zinc chromate (in general commercial use as "Zinc Yellow" pigment) is widely employed in commercial paint and coating formulations, e.g., alkyd and latex paint formulations, but unfortunately it is characterized by a relatively high toxicity, which has limited its use in practice. A large number of organic protective coatings, and corrosion inhibitor pigments/additives for such coating compositions, have been developed.

U.S. Pat. No. 4,246,030 discloses a corrosion inhibitor for metals exposed to water, comprising a water soluble carboxylic acid and/or the salt thereof containing at least one hydroxyl group per molecule, and an amino alkylene phosphonic acid or derivative thereof, together with dispersing agents and other inhibitors such as molybdates, azoles and various inorganic metal compounds, including zinc oxide. The disclosed compounds include alkali metal salts of N-hydroxy ethylenediamine triacetic acid.

U.S. Pat. No. 4,217,142 discloses the use of magnesium azelate as a rust inhibitor for metal paints, preferably in combination with a basic oxide such as magnesium oxide. The patent specifically discloses that lead, calcium and zinc azelates in inert vehicles are unsatisfactory as corrosion inhibitors.

U.S. Pat. No. 2,816,051 discloses corrosion inhibitors which may be incorporated in primer coatings or volatile solvents for application to corrodible metals. The disclosed corrosion inhibitors are organic esters of certain acidic oxides of metals, including chromic acid, orthovanadic acid, metavanadic acid and molybdic acid.

A corrosion-inhibiting material for use in a coating composition is disclosed in U.S. Pat. No. 4,212,674, which comprises a fine particulate material such as natural crystalline calcium carbonate on which is coated a film of fatty amine or a fatty amine salt; the patent discloses that other conventional fillers, including kaolin, may be employed.

A surface treated filler material is disclosed in U.S. Pat. No. 4,191,670, as having utility in the preparation of emulsion paints, to improve the scrub resistance of such paints. The fillers, include natural and precipitated carbonates and silica compounds such as silicate including kaolin, mica and calcium. Such fillers are treated with a mixture of saturated and unsaturated aliphatic carboxylic acids. Such treated mineral fillers are disclosed to be particularly suited for water-based coating systems including acrylates and acrylic acid co-polymer systems.

U.S. Pat. No. 4,427,448 discloses a removable, oil-based corrosion inhibitor containing an aliphatic primary amine, an organic fatty acid plus an organotin compound and a glycolester.

Corrosion inhibitor for water-based latex paints designed to combat both pre-and post-drying rusting is disclosed in U.S. Pat. No. 4,243,417. The corrosion inhibitor has a formula $M(Z)_xAn$, where M is a metal cation, An is a corrosion-inhibiting anion, and Z is a complexing volatile component, such as amino or alkylamino.

U.S. Pat. No. 3,306,908 discloses reaction products of high molecular weight hydrocarbon succinic acid compounds, amines and heavy metal compounds such as zinc or zinc oxide, which are useful as paint additives and impart corrosion-inhibiting characteristics. U.S. Pat. No. 3,163,603 discloses amide and imide derivatives of metal salts of substituted succinic acids and their use as corrosion inhibitors.

Rust-preventative paint compositions are disclosed in U.S. Pat. No. 3,876,574, which comprise polycarboxylic acids and compounds of metals such as zinc.

U.S. Pat. No. 2,689,828 discloses a mineral oil composition containing a corrosion inhibiting agent prepared from a phthalic acid, an alkyl-substituted phthalic acid or its anhydride, and a primary, secondary or tertiary amine.

Although as shown by the foregoing, numerous anticorrosion coating compositions and corrosion inhibitor additives have been developed in the prior art, there is nonetheless a continuing need for the development of improved corrosion-inhibiting additives and coating compositions containing the same, which are non-toxic or of reduced toxicity relative to the zinc chromate additive and compositions which are in commercial use.

SUMMARY OF THE INVENTION

In accordance with the present invention, there is provided a coating composition having utility for protecting metallic substrates susceptible to corrosion, comprising:
  (a) a film-forming vehicle; and
  (b) a corrosion-inhibiting amount of amine-complexed zinc salt of an organic diacid selected from the group consisting of (i) dicarboxylic acids, (ii) diphenols, and (iii) phthalic acids.

Another aspect of the invention provides a coating composition having utility for inhibiting marine growth, such as barnacles and algae, on substrates and containing a marine growth-inhibiting amount of a composition selected from (i) or (ii) above.

Other aspects of the invention provide the following features, alone or in combination: the film-forming vehicle may be selected from the group consisting of alkyds, latexes and linseed oils. The amine may be selected from the group consisting of alkylenediamines, polyalkylamines and polyalkanolamines, and preferably a C₂–C₃ diamine; the organic acid may be a dicarboxylic acid of the formula

HOOC—(CH₂)ₙ—COOH wherein n is an integer of from 1 to 20, preferably from 2 to 12; and the amine-complexed zinc salt of the organic diacid may have the structural formula ZnA$_x$·B$_y$ wherein A is the organic diacid residue, B is the amine, x is between 0.6 and 1.0, and y is between 0.01 and 1.0.

Still other aspects of the invention provide that the amine-complexed zinc salt of the organic diacid is a reaction product of zinc oxide, the amine and the organic diacid, which may be present in the reaction in an approximately 1:1:1 molar ratio. In one embodiment, the molar ratio of the organic acid to the diamine in the reaction is from about 1.0 to 1.2.

The coating composition may comprise, in yet another aspect of the invention, a mineral filler selected from the group consisting of bentonite, kaolin, mica and wollastonite, preferably kaolin and most preferably delaminated kaolin, and the amine-complexed zinc salt of the organic diacid may be distended on said mineral filler.

Related aspects of the invention include (i) a method of protecting a metallic substrate susceptible to corrosion comprising applying to such substrate a coating of the aforementioned compositions, and curing the same, and (ii) a metallic substrate coated with a cured film of such coating composition.

In another aspect, the invention provides an amine-complexed zinc salt of an organic diacid, in distended form on a mineral filler, and a method for making such zinc salt/mineral filler composition, comprising the steps of:

(a) dispersing the mineral filler in an aqueous medium to form a slurry thereof;
(b) adding to such slurry (i) zinc oxide, (ii) the amine, and (iii) the organic diacid under reaction conditions including an elevated temperature, preferably at least about 90° C., which is at least sufficient to yield the amine-complexed zinc salt of the organic diacid in distended form on the mineral filler in the slurry;
(c) cooling the slurry to precipitate therefrom the amine-complexed zinc salt; and
(d) recovering the mineral filler with the amine-complexed zinc salt precipitate thereon.

Other aspects of the invention include one or more of the following embodiments: the recovered precipitate of step (d) may be dried and pulverized to form a particulate mineral filler having the amine-complexed zinc salt distended thereon; an anticorrosion coating composition may be made by a method comprising dispersing in a film-forming vehicle a corrosion-inhibiting amount of the aforesaid particulate mineral filler; in the method of producing the aforesaid amine-complexed zinc salt of an organic diacid, the zinc oxide, amine, and organic diacid may be added to the slurry in the aforesaid step (b) in amounts proportioned to provide a predetermined concentration of the amine-complexed zinc salt, such that the weight ratio of the amine-complexed zinc salt to the mineral filler in the precipitate recovered in the aforesaid step (d) is from about 0.25 to about 1.2. Preferably, the amine is selected from alkylenediamines, polyalkylamines, and polyalkanolamines; the organic diacid is preferably selected from the group consisting of (i) dicarboxylic acids, (ii) diphenols, and (iii) phthalic acids; and in the aforesaid step (b), the zinc oxide and organic diacid are added to the slurry to form a first reaction product, followed by addition thereto of the amine to form the amine-complexed zinc salt of the organic diacid as a second reaction product.

Yet another aspect of the invention provides amine-complexed zinc salts of an organic diacid selected from the group consisting of unchlorinated diphenols, unchlorinated sulfonyldiphenols, and phthalic acids. Such aspect of the invention includes more specifically amine-complexed zinc salts of the above described formulas, especially C₂–C₃ alkylene diamine-complexed zinc salts of thiodiphenol or sulfonyldiphenol, and ethylene diamine-complexed zinc salts of phthalic acids.

As used herein, "phthalic acids" is intended to be broadly construed to include phthalic acid, isophthalic acid and/or terephthalic acid.

The term "distended" in reference to the amine-complexed zinc salts of the invention on a mineral filler means that the complexed zinc salt is dispersed on the mineral filler surface and is associatively bonded thereto.

Generally, the present invention is seen to provide a corrosion inhibitor additive for coating compositions, which additive is readily and easily made and is characterized by satisfactory toxicity characteristics relative to zinc chromate pigments and compositions. The present invention also provides a corrosion inhibitor additive of such type in a distended form on a mineral filler, whereby such additive may be readily and uniformly dispersed in a coating composition containing the same, to provide uniform and effective anticorrosion activity. Another aspect of the present invention resides in the fact that at least some of the compounds of the invention have demonstrated efficacy as antimarine fouling pigments in alkyd paint formulations in addition to efficacy as corrosion-inhibiting pigments.

Other aspects of the invention are defined in the appended claims and will be apparent from the detailed description below.

DETAILED DESCRIPTION OF THE PREFERRED EMBODIMENTS

Figure 1:
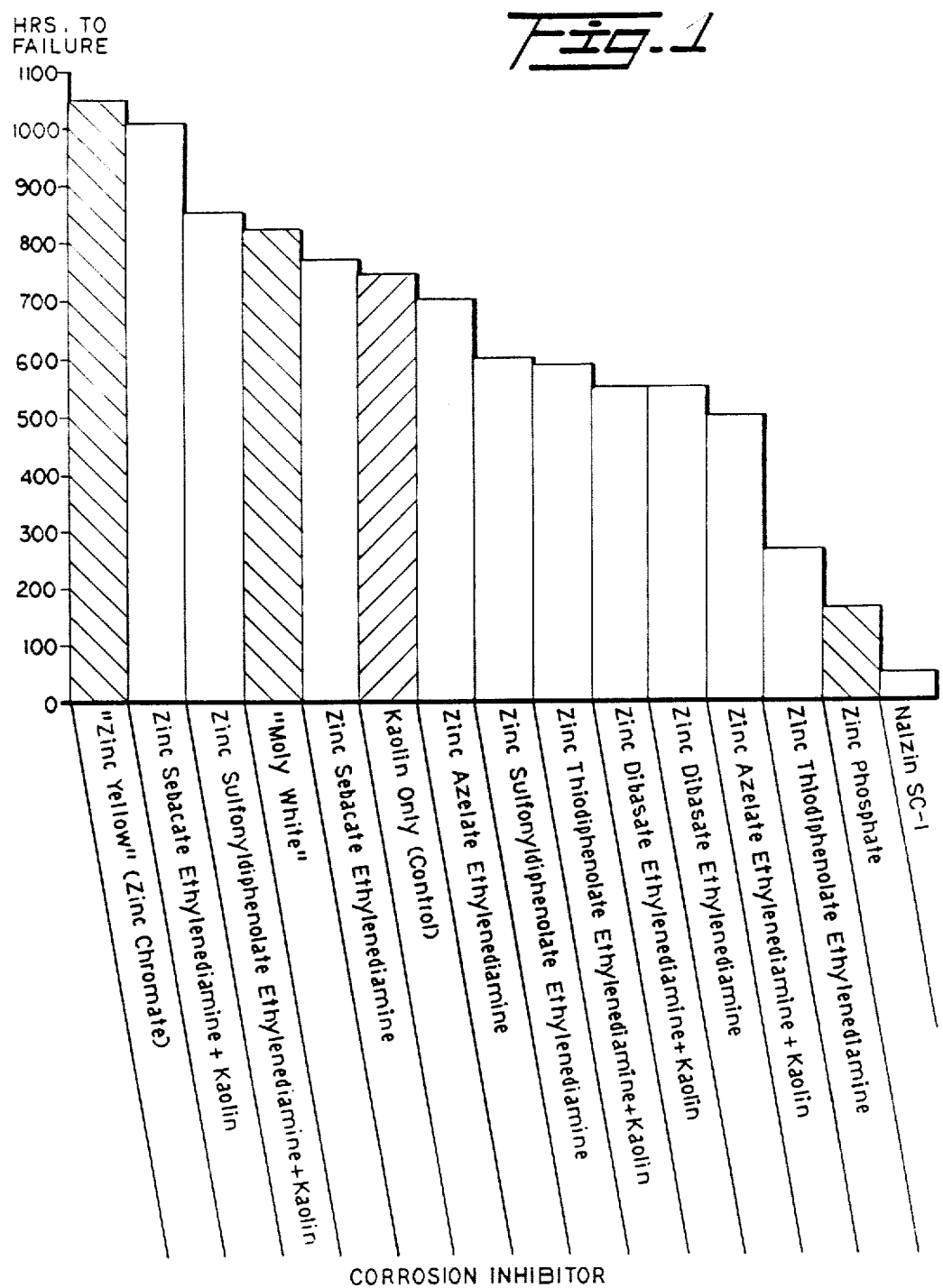
FIGS. 1 and 3 are bar graphs showing hours to failure in a salt spray test of alkyd formulations containing various corrosion inhibitors.

The anticorrosion coating compositions of the present invention comprise a film-forming vehicle which may comprise a suitable coating formulation compatible with the amine-complexed zinc salt of an organic diacid selected from the group consisting of (i) dicarboxylic acids, (ii) diphenols, and (iii) phthalic acids, and may comprise any suitable formulation components generally employed in the art therefor, such as binders, solvents, pigments, stablizers, extenders, fillers and additives. Particularly preferred in practice, however, are film-forming vehicles such as alkyds, latexes and linseed oils.

The amine employed in complex with the zinc salt in the present invention may be any suitable amine such as alkylenediamines, polyalkylamines or polyalkanolamines, wherein the alkylene, alkyl and alkanol moieties of these amines may be either straight-chained or branched, suitably comprising from 1 to 8, or more, carbon atoms. Particularly preferred alkylenediamines are ethylenediamine and propylenediamine. A suitable polyalkyl amine is diethylamine, and triethanolamine is usefully employed as a suitable polyalkanolamine.

Various dicarboxylic acids may be employed to form the amine-complexed zinc salt of the present invention, including for example, straight-chain dicarboxylic acids of the formula $HOOC-(CH_2)_n-COOH$, wherein n is an integer of from 1 to 20. Preferred dicarboxylic acids include those of the same formula wherein n is from 2 to 12. The dicarboxylic acids employed to form the amine-complexed zinc salts in the present invention may usefully include mixtures of compounds, such as Dibasic Acid (DuPont, Wilmington, Delaware), which is a commercially available mixture of $C_{10}-C_{12}$ alkylene dicarboxylic acids.

Examples of amine-complexed zinc salts of dicarboxylic acids useful as corrosion inhibitor additives in the practice of the present invention include:
Zinc succinate ethylenediamine
Zinc glutarate ethylenediamine
Zinc adipate ethylenediamine
Zinc adipate propylenediamine
Zinc azelate ethylenediamine
Zinc sebacate ethylenediamine
Zinc dibasate ethylenediamine
Zinc dibasate propylenediamine
Zinc dibasate diethylamine
Zinc dibasate triethanolamine
Zinc dodecanedioate ethylenediamine
Zinc dodecanedioate diethylamine
Zinc dodecanedioate triethanolamine The diphenols useful in the amine-complexed zinc salts in the present invention include phenols such as thiodiphenols and sulfonyldiphenols, such as 4,4'-thiodiphenol and 4,4'-sulfonyldiphenol. Preferred amines employed to form the amine-complexed zinc salts of such diacids include $C_2-C_3$ alkylenediamines, illustrated by compounds such as zinc thiodiphenolate ethylenediamine, zinc sulfonyldiphenolate ethylenediamine, and zinc sulfonyldiphenolate propylenediamine.

Phthalic acids, such as one or more of phthalic acid, isophthalic acid and terephthalic acid, may likewise be employed to form the amine-complexed zinc salts of the present invention. Illustrative of such compounds are zinc phthalate ethylenediamine, zinc isophthalate ethylenediamine, and zinc terephthalate ethylenediamine.

The amine-complexed zinc salts of the present invention may usefully be prepared as a reaction product of zinc oxide, the amine and the organic diacid, with the reaction suitably being carried out in aqueous medium at elevated temperature, e.g., a temperature of 90° C. or higher. The zinc oxide, amine and organic diacid reactants may be concurrently added to the reaction system, but preferably the zinc oxide is first reacted with one of the diamine and organic diacid components, followed by addition and reaction with the other component. Most preferably, the zinc oxide is first reacted with the organic diacid, following which the amine reactant is added and reacted; this order of addition was generally found to produce the highest yields of amine-complexed zinc salt product. Based on stoichiometric considerations, when a diamine is used as the amine reactant, it is satisfactory to provide the zinc oxide, diamine or organic diacid reactants in the reaction system in an approximately 1:1:1 ratio. In practice, the molar ratio of the organic diacid to the diamine in the reaction system may range from about 1.0 to about 1.2.

After reaction of the zinc oxide, amine or organic diacid has taken place, e.g., 30 minutes to one hour or more, the aqueous reaction medium may be cooled, as by ice bath cooling of the reaction vessel, to complete the precipitation therefrom of the amine-complexed zinc salt product. The precipitated product may then be recovered by filtration and drying under ambient or elevated temperature conditions. The dried zinc salt complex then may be pulverized, such as by micropulverization to a finely divided state, e.g., to a size which will pass through a screen with openings of about 0.02 inch, to provide the product salt complex as a particulate or powder for use in the coating compositions of the invention.

Although the prior art has taught various reactions of acid, base and metal to obtain metal complexes, e.g., U.S. Pat. Nos. 3,306,908, 3,544,609, 3,551,466, 3,557,171 and 3,493,508, the amine-complexed zinc salts of organic diacids selected from the group consisting of unchlorinated thiodiphenols, unchlorinated sulfonyldiphenols, and phthalic acids are believed not to have been suggested in the art. In the case of the diphenols, chlorine or other halogen substituents are preferably avoided, since the presence of such halogen substituents in the product amine-complexed zinc salt generally would be expected to have a significantly adverse effect, insofar as the corrosion inhibition characteristics of the salt-amine complex are concerned.

The amine-complexed organic diacid zinc salts employed in the coating compositions of the invention suitably have a formula as set forth below:

$$ZnA_xB_y$$

wherein A is the residue of the organic diacid formed by the removal of at least one of the acidic hydrogens from the carboxyl substituents of the dicarboxylic acids or phthalic acids or, in the case of the diphenolate compounds, the hydrogens of the hydroxyl groups of such compounds. B is the amine, x is between 0.6 and 1.0 and y is between 0.01 and 1.0. Although the preferred molar ratio of zinc oxide, organic diacid and amine employed to form the amine-complexed zinc salts is, as indicated, preferably about 1:1:1, it has been found that the molar ratio of zinc to organic diacid residue to amine in the complexed salt product is such that the molar ratio of diacid to zinc is generally less than but nonetheless approximately 1, while the ratio of amine to zinc in the complexed salt is generally significantly less than 1. In addition, it has been found that in the zinc salt-amine complex formation reaction, an excess of the organic diacid relative to the amine reactant results in improved yields of the zinc salt-amine complex product. For this reason, it is desirable in many instances to provide a reactant molar ratio of organic diacid to amine in the range of from about 1.0 to 1.25. In general, the amine-complexed zinc salt of the invention should have a relatively high amine content, since there is a general trend of improving corrosion inhibition with increasing amine content in the salt complex. However, excessive amine content promotes degradation of the coating composition containing the zinc salt complex as a corrosion inhibitor. Elemental analyses of various illustrative compounds of the invention are set forth in Table I below, wherein TDP means thiodiphenolate, EN means ethylenediamine, SDP means sulfonyldiphenolate, A means azelate, S means sebacate, D means dibasate, DAP means diaminopropane, DMA means dimethylamine and DEA means diethylamine.

TABLE I

| Compound | Elemental Analysis $Zn_xB_y$ |
|---|---|
| Zinc Thiodiphenolate Ethylenediamine | $Zn_{1.0}TDP_{0.91}EN_{0.87}$ |
| Zinc Sulfonyldiphenolate Ethylenediamine | $Zn_{1.0}SDP_{1.0}EN_{0.58}$ |
| Zinc Azelate Ethylenediamine | $Zn_{1.0}A_{0.88}EN_{0.14}$ |
| Zinc Sebacate Ethylenediamine | $Zn_{1.0}S_{0.79}EN_{0.15}$ |
| Zinc Dibasate Ethylenediamine[1] | $Zn_{1.0}D_{0.86}EN_{0.15}$ |
| Zinc Thiodiphenolate-1,2-Diaminopropane | $Zn_{1.0}TDP_{1.0}$—1,2-$DAP_{0.23}$ |
| Zinc Dibasate-1,2-Diaminopropane | $Zn_{1.0}D_{1.0}$—1,2-$DAP_{0.6}$ |
| Zinc Dibasate Dimethylamine | $Zn_{1.0}D_{0.68}DMA_{0.03}$ |
| Zinc Dibasate Diethylamine | $Zn_{1.0}D_{0.86}DEA_{0.10}$ |
| Zinc Dibasate-1,2-Diaminopropane | $Zn_{1.0}D_{0.97}$—1,3-$DAP_{0.19}$ |

[1] In this as in subsequent table entries, Dibasate refers to the organic diacid residue derived from Dibasic Acid (E. I. du Pont de Nemours & Company, Wilmington, Delaware), a commercially available mixture of linear $C_{10}$-$C_{12}$ alkylene dicarboxylic acids.

As shown by the above representations in Table I, derived by conventional elemental analyses of the listed compounds, the molar ratio of the organic diacid residue to Zn(II), ranged from 0.68 in the case of zinc dibasate dimethylamine to 1.0 in the case of zinc sulfonyldiphenolate ethylenediamine, zinc thiodiphenylate-1,2-diaminopropane, and zinc dibasate-1,2-diaminopropane. The molar ratio of the amine to the zinc, on the other hand, ranged from 0.03 in the case of zinc dibasate dimethylamine, to 0.87 in the case of zinc thiodiphenolate ethylenediamine.

In various embodiments of the anticorrosion coating composition of the present invention, it has been found advantageous to employ the amine-complexed zinc salt in combination with a mineral filler, which may, for example, comprise wollastonite or mica or a clay such as bentonite or kaolin. In a particularly preferred embodiment of the present invention the amine-complexed zinc salt is utilized in a distended form on the mineral filler. Although any of the aforementioned, or other, mineral fillers may be employed for such purpose, a particularly preferred mineral filler is kaolin, preferably in a delaminated form. The advantage of kaolin and other similar mineral fillers in such delaminated form derives from the fact that the platelet (mica-like) structure thereof may increase the effective path length that moisture or other atmospheric corrosives must travel to reach the metallic substrate on which the coating composition containing the filler distended thereon is coated. One such commercially available delaminated kaolin material is ASP-752 (Engelhard Corporation), which has particles in the shape of thin flat plates with an average particle size of 1.8 microns and 0.01% greater than 44 microns and an oil absorption value, as measured by ASTM D281-31, of 40 grams of oil per 100 grams of pigment.

The amine-complexed zinc salt of the organic diacid may be produced in distended form on a mineral filler of the aforementioned type, by first dispersing the mineral filler in the aqueous medium to form a slurry thereof. To the slurry then may be added the zinc oxide, the amine and the organic diacid. As previously mentioned it is generally advantageous to add the zinc oxide to one of the amine and diacid reactants, with the other being added subsequently so that the zinc salt complex formation reaction takes place in two steps. In some instances, it may be desirable to add the zinc oxide reactant to the organic diacid first, following the reaction of which the amine constituent is added to the reaction; such sequence of acid addition followed by amine (base) addition has been found advantageous in some instances in producing improved yield of the zinc salt product.

Following reaction, which may be carried out at a temperature of about 90° C. or higher for a period of time from about 30 minutes to about 2 hours depending on the rate of reactant addition and specific temperature level, the slurry is cooled to complete the precipitation therefrom of the amine-complexed zinc salt which is thereby distended upon the mineral filler particles. From the cooled slurry, the precipitated zinc salt complex/mineral filler product may be recovered by filtration followed by drying and micropulverization to yield the particulate corrosion-inhibiting pigment in appropriate form for dispersing and/or grinding in the coating composition formulation. The relative amounts of organic diacid, zinc oxide and amine may be as previously described herein.

In preferred practice, the zinc oxide, amine and organic diacid are added to the slurry in amounts proportioned to provide a predetermined concentration of the amine-complexed zinc salt, such that the weight ratio of the amine-complexed zinc salt to the mineral filler in the product mineral filler/salt complex is from about 0.25 to about 1.2. In practice, a 50/50 weight ratio of mineral filler and zinc salt complex has been found satisfactory.

In general, the amine-complexed zinc salt corrosion inhibitors of the present invention meet the following criteria:

1. Reaction yield of at least 25% from the zinc oxide/organic diacid/amine reaction;
2. A corrosion current, $I_{corr}$, of less than 100 microamps;
3. A corrosion potential, $E_{corr}$, of less than minus 700 millivolts;
4. A pH greater than about 7;
5. Reasonable cost;
6. Low toxicity; and
7. Moderate water solubility.

The coating compositions of the present invention have broad utility for protecting metallic substrates susceptible to corrosion, including ferrous substrates such as iron and steel as well as copper, magnesium, aluminum, and alloys thereof as well as other conventional metals employed in structural or substrate applications where corrosion may occur due to contact by atmospheric moisture, water or other corrosives normally present in urban or industrial environments.

The advantages and utility of the invention are shown by the following examples of illustrative character, wherein all parts and percentages are by weight, unless otherwise noted.

For ease of reference in the ensuring discussion, illustrative amine-complexed zinc salts of the present invention as tested in the subsequent examples are set forth in Table II below, with each compound referenced to a compound number.

TABLE II

Amine-Complexed Zinc Salts Of Organic Diacids

| Compound No. | Compound |
|---|---|
| 1 | Zinc Succinate Ethylenediamine |
| 2 | Zinc Glutarate Ethylenediamine |
| 3 | Zinc Adipate Ethylenediamine |
| 4 | Zinc Adipate Propylenediamine |
| 5 | Zinc Azelate Ethylenediamine |
| 6 | Zinc Sebacate Ethylenediamine |
| 7 | Zinc Dibasate Ethylenediamine |
| 8 | Zinc Dibasate Propylenediamine |
| 9 | Zinc Dibasate Diethylamine |
| 10 | Zinc Dibasate Triethanolamine |
| 11 | Zinc Dodecanedioate Ethylenediamine |
| 12 | Zinc Dodecanedioate Diethylamine |
| 13 | Zinc Dodecanedioate Triethanolamine |
| 14 | Zinc Thiodiphenolate Ethylenediamine |
| 15 | Zinc Sulfonyldiphenolate Ethylenediamine |
| 16 | Zinc Sulfonyldiphenolate Propylenediamine |
| 17 | Zinc Phthalate Ethylenediamine |
| 18 | Zinc Isophthalate Ethylenediamine |
| 19 | Zinc Terephthalate Ethylenediamine |
| 20 | Zinc Thiodiphenolate Propylenediamine |
| 21 | Zinc Dibasate Dimethylamine |
| 22 | Zinc Quinizarinate Ethylenediamine |
| 23 | Zinc Dibasate Pyridine |
| 24 | Zinc Dibasate Piperidine |
| 25 | Zinc Dibasate N—Phenylanthraniline |
| 26 | Zinc Azelate Propylenediamine |

EXAMPLE I

Various illustrative amine-complexed zinc salts of the present invention were evaluated relative to the criteria discussed above for suitable compounds, including a reaction yield of at least 25%, a corrosion current of less than 100 microamps, a corrosion potential of more than minus 700 millivolts, and a pH greater than about 7. In each instance, the amine-complexed zinc salts were prepared by reaction of 0.05 moles of each of the zinc oxide, organic diacid and amine reactants, at the reaction temperature and reaction time (minutes) conditions set forth in Table III below. This Table also sets forth for each compound the corrosion current, corrosion potential, pH and reaction yield of the amine-complexed zinc salt product.

TABLE III

| Cmpd No. | Reaction Conditions (min.) | Reaction Conditions (°C.) | Product Yield, % | Corrosion Curr.[1] | Corrosion Pot.[2] | pH |
|---|---|---|---|---|---|---|
| 14 | 30 | 96 | 89 | 52.5 | −570 | 8.60 |
| 15 | 30 | 96 | 70 | 170 | −592 | 7.67 |
| 5 | 30 | 96 | — | 82 | −667 | 6.78 |
| 6 | 30 | 97 | — | 170 | −462 | 6.8 |
| 7 | 30 | 90 | — | 86 | −625 | 7.24 |
| 20 | 90 | 95 | 81.2 | 46 | −560 | 8.18 |
| 8[3] | 90 | 95 | 49.1 | 90 | −570 | 7.55 |
| 21 | 120 | 90 | 44 | 82 | −610 | 6.85 |
| 9 | 120 | 90 | 77 | 30 | −570 | 7.0 |
| 22 | 30 | 95 | 90 | 84 | −570 | 7.75 |
| 8[4] | 90 | 95 | 52.1 | 48 | −590 | 7.35 |
| 23 | 90 | 95 | 45 | 60 | −550 | 7.0 |
| 24 | 90 | 95 | 47.4 | 40 | −610 | 7.1 |
| 10 | 30 | 95 | 52 | 93 | −580 | 7.2 |
| 25 | 30 | 95 | 87.8 | — | — | — |
| 3 | — | — | — | 78 | — | — |
| 9[5] | — | — | — | 177 | — | — |
| 11 | — | — | — | 130 | — | — |
| 12 | — | — | — | 197 | — | — |
| 17 | — | — | — | 83 | — | — |

[1] Curr. = current in microamps
[2] Pot. = potential in millivolts
[3] 1,2-diaminopropane compound
[4] 1,3-diaminopropane compound
[5] Second test of compound No. 9; note first test value of 30 microamps In the above table, the corrosion data presented as corrosion current and corrosion potential were determined by electrochemical testing. The specific test used was the Tafel Plot, which scans ±0.250 volt about the corrosion potential $E_{corr}$. From this plot is determined the corrosion current $I_{corr}$, as is well known to those skilled in the art. Simply stated, the corrosion current $I_{corr}$ is directly proportional to the rate of corrosion that is occurring on the test specimen. The higher the corrosion current value, the more corrosion is occurring on the test sample. Empirical results indicate that a value of corrosion current of about 100 microamps or less is consistent with good levels of corrosion protection in use. The corrosion potential of the test specimens was measured against a saturated calomel electrode, a technique well known to those skilled in the art.

The electrolyte employed to determine the corrosion current and corrosion potential values by the above procedure was a simulation of acid rain encountered at urban industrial locations, as determined from the relevant technical literature. The electrolyte compositions specifically employed in these tests is set forth in Table IV below; the pH of this electrolyte was about 4.2.

TABLE IV

| Component | Electrolyte Composition Concentration, Grams/Liter |
|---|---|
| NaCl | 1.09 |
| $MgSO_4.7H_2O$ | 1.81 |
| $KNO_3$ | 0.452 |
| $NH_4Cl$ | 0.551 |
| $NaNO_3$ | 0.151 |
| $H_2SO_4$ | 0.0034 |

The test metal used for each of the electrochemical tests was a low carbon steel SAE-1020 hot rolled bar, machined to a uniform 7.86 millimeter diameter and 18.9 millimeter length, providing an exposed surface area of 5.16 square centimeters. In each instance, the Tafel Plot was obtained on the simulated rain solution saturated with the pigment being tested.

The data in Table III showed that the compounds of the present invention were obtained in all cases at desirable yield levels, consistent with the aforementioned criterion of at least 25% yield. In terms of the criterion level of corrosion current of about 100 microamps or less, all of the compounds listed in Table III achieved such low corrosion current level with the exception of zinc sulfonyldiphenolate ethylenediamine (compound 15), zinc sebacate ethylenediamine (compound 6), zinc dibasate diethylamine (compound 9, second test; note that the first test of the same compound gave a corrosion current of 30 microamps), zinc dodecanedioate diethylamine (compound 12) and zinc dodecanedioate ethylenediamine (compound 11). The corrosion potential criterion of at least minus 700 millivolts for "good" corrosion inhibitors was met by all of the Table III compounds tested. Similarly, the pH criterion for good corrosion inhibitors, i.e., a pH greater than about 7, was met generally by all of the compounds tested.

For purposes of comparison, electrochemical testing likewise was performed according to the above-described procedure for various commercial corrosion inhibitive pigments. The data for such comparative testing are set forth in Table V below.

TABLE V

Electrochemical Test Results For Commercial Pigments

| Pigment | Corrosion Curr. microamps* | Potential mv** | pH |
|---|---|---|---|
| Busan-11 M1 | 5.6 | −522 | 9.3 |
| Nalzin SC-1 | 36 | −540 | 7.2 |
| Moly-White 212 | 110 | −566 | 8.2 |
| Halox CW-221 | 65 | −473 | 8.9 |
| Zinc Chromate | 12 | −515 | 6.6 |
| Blank+ | 740 | −670 | 4.2 |

*Probe surface 5 cm$^2$
**Against saturated calomel electrode
+Average of 4 determinations

EXAMPLE II

As indicated, one of the criteria for good corrosion-inhibitor additives is a moderate water solubility. Ideally, the corrosion inhibitor should have a solubility low enough so that blistering and delamination of the paint film does not occur. Conversely, the solubility should be sufficiently high to afford protection of the metal substrate to which the coating composition containing such inhibitor is applied. Generally, a low solubility is consistent with high durability of the coating film containing such corrosion inhibitor.

A modified form of the solubility test procedure set forth in ASTM-D1766 was performed on various illustrative amine-complexed zinc salts of the present invention, and the results are set forth in Table VI below. Table VII below lists corresponding solubility data for commercially available anticorrosion-inhibiting pigments.

TABLE VI

Solubility Data For Amine-Complexed Zinc Salts Of Organic Diacids

| Compound No. | Solubility, g/100 cc H$_2$O | Description(a) |
|---|---|---|
| 1 | .39 | SS |
| 2 | .16 | SS |
| 3 | .15 | SS |
| 5 | .21 | SS |
| 6 | .18 | SS |
| 7 | .32 | SS |
| 8 | .16 | SS |
| 9 | .02 | PINS |
| 11 | .015 | PINS |
| 13 | .001 | PINS |
| 14 | .03 | PINS |
| 15 | .39 | SS |
| 17 | .02 | PINS |
| 18 | 1.13 | MS |
| 19 | .66 | SS |

(a)PINS = practically insoluble (<.1 g/100 cc H$_2$O)
SS = slightly soluble (.1 to 1 g/100 cc H$_2$O)
MS = moderately soluble

TABLE VII

Solubility Data For Commercially Available Corrosion-Inhibitor Pigments

| Commercial Pigment | Solubility g/100 cc H$_2$O | Description(a) |
|---|---|---|
| Busan | 0.35 | SS |
| Zinc Yellow | 0.20 | SS |
| Nalzin | 0.10 | SS |
| Moly White | 0.01 | PINS |

(a)SS = Slightly soluble (.1 to g/100 cc H$_2$O)
PINS = Practically insoluble (<.1 g/100 cc H$_2$O)

As shown by the data in Tables VI and VII, the amine-complexed zinc salts of the present invention generally had solubility characteristics consistent with the commercial pigments, with the exception of zinc dibasate diethylamine (compound 9), zinc dodecanedioate ethylenediamine (compound 11), zinc dodecanedioate triethanolamine (compound 13), zinc thiodiphenolate ethylenediamine (compound 14) and zinc phthalate ethylenediamine (compound 17).

EXAMPLE III

A further criterion for effective corrosion-inhibitor compounds, as discussed herein above, is low toxicity. A primary objective of the present invention is to provide corrosion-inhibitor compounds which are generally comparable in performance characteristics to the widely used "Zinc Yellow" zinc chromate pigment but which have significantly reduced toxicity.

Illustrative corrosion inhibitor compounds of the present invention were tested for toxicity characteristics by three separate tests: (1) acute oral toxicity, (2) primary skin irritation, and (3) Draize eye irritation. Data obtained in such testing are shown in Table VIII below, together with toxicity-related data for commercial corrosion-inhibitor pigments.

TABLE VIII

| Compound No. | Acute Toxicity Test Results | |
|---|---|---|
| Oral (5 g/kg in Corn Oil) | | |
| 6 | 0% | mortality |
| 15 | 10% | mortality |
| 14 | 100% | mortality |
| 9 | 0% | mortality |
| 3 | 0% | mortality |
| 17 | 0% | mortality |
| Skin Irritation (0.5 g in Saline Paste) | | |
| 6 | 0.13 | score-minimally irritating |
| 15 | 0.08 | score-non-irritating |
| 3 | 0.42 | score-minimally irritating |
| 17 | 0.00 | score-non-irritating |
| Eye Irritation (100 mg) | | |
| 6 | 37.2 | score-severely irritating |
| 15 | 31.0 | score-severely irritating |
| 14 | 53.7 | score-extremely irritating |
| 9 | 5.5 | score-mildly irritating |
| 3 | 19.0 | score-moderately-irritating |

Commercial Pigments
Red lead LDLo = 1g/kg (oral)
Zinc chromate TDLo = 12 mg/kg (intratracheal)
Moly White LD$_{50}$ = 50 g/kg (oral)
Busan LD$_{50}$ = 850 mg/kg (oral)

The data show that the only pigment of the present invention which was tested and indicated to have unacceptable toxicity characteristics was zinc thiodiphenolate ethylenediamine (compound 14).

EXAMPLE IV

In this Example, various illustrative corrosion-inhibitor compounds of the present invention were synthesized, some being formed in the reaction system with a commercially available kaolin mineral filler in delaminated form (ASP-752, Engelhard Corporation, Menlo Park, N.J.) being present in the reaction system, whereby the amine-complexed zinc salt was produced in distended form on the delaminated kaolin filler.

The synthesis procedure in general terms for all corrosion-inhibitor compounds was as follows. The metal, in the form of zinc oxide, was mixed with the amine constituent in an aqueous slurry. The organic diacid then was slowly introduced. The amounts of each reagent was always maintained at a 1:1:1 molar ratio of zinc:organic diacid:amine. (In some cases the order of organic diacid and amine addition was sometimes reversed to improve yield.) The reaction was carried out at 90° C. for one hour over a water bath. After completion, the reaction volume was cooled to 4° C., the product was filtered, washed, oven-dried at 60° C. for 1-2 hours and micropulverized.

If the corrosion inhibitor composition comprised the delaminated kaolin filler, the reaction was performed as described above, except that the kaolin material was the first ingredient in the reaction vessel. The kaolin in such cases was predetermined in amount so that the final corrosion-inhibitor product would be 50% amine-complexed zinc salt (as the active pigment) and 50% kaolin. Despite such predetermined amounts, the reaction yields for the best composite amine-complexed zinc salt/mineral filler corrosion inhibitors indicated that the zinc salt was about 30% by weight of the composite and kaolin about 70% by weight, based on the assumption that no mineral filler is lost during reaction. Table IX lists yields of all corrosion inhibitor compounds and composites.

TABLE IX

| Corrosion-Inhibitor Compounds And Composites | | | |
|---|---|---|---|
| Compound No. (M = Mineral Filler) | % Yield | Compound No. (M = Mineral Filler) | % Yield |
| 3 | 33 | 13 | 42 |
| 3 | 45 | 14 | 89 |
| 4 | 43 | 14 | 96 |
| 26 | 45 | 15 | 60 |
| 6 | 57 | 15 | 86 |
| 6 | 44 | 15 | 81 |
| 6 | 59 | 16 | 77 |
| 8 + M[(1)] | 71 | 17 | 44 |
| 12 + M[(2)] | 76 | 17 + M[(3)] | 70 |
| 10 | 60 | 18 | 33 |
| 11 | 66 | 18 | 28 |
| 11 | 65 | 19 | 62 |
| 12 | 53 | 19 | 85 |

[(1)]22% active pigment in composite
[(2)]26% active pigment in composite
[(3)]28% active pigment in composite Recognizing that the objective criterion for good corrosion-inhibitor compounds involved a yield of at least 25%, the data in Table IX show that all of the compounds of the present invention represented in such table met the criterion. The composite pigments, i.e., zinc dibasate propylenediamine (compound 8), zinc dodecanedioate diethylamine (compound 12) and zinc phthalate ethylenediamine (compound 17), all in composition with delaminated kaolin as the mineral filler, demonstrated yields of 70% and above of the product composite.

EXAMPLE V

In this set of tests, illustrative corrosion-inhibitor compounds of the present invention were incorporated in acrylic latex and alkyd vehicles. The acrylic latex primer was formulated with MV-23 latex (Rohm & Haas, Philadelphia, Pennsylvania) at 26% PVC (pigment content in dried film, by volume) and 38% NVV (non-volatile content of paint, by volume); the details of such formulation are set forth in Table X below. The alkyd primers were formulated with McCloskey Varkyd 1S31-50E medium oil alkyd at 38% PVC and 45% NVV; the details of this formulation are set out in Table XI below.

TABLE X

| | Grams |
|---|---|
| Grind | |
| Water | 56.1 |
| Colloid 681F (Colloids) | 0.88 |
| NH$_4$OH (28%)(Carco Chemicals Corp.) | 2.7 |
| Tamol 850 (20%)(Rohm & Haas) | 3.53 |
| Triton CF10 (Rohm & Haas) | 1.1 |
| Chem Carb 11 (Engelhard Corporation) | 9.01 |
| Kadox 515 (Gulf & Western Natural Resources Group) | 4.3 |
| Titanox 2160 (NL Industries) | 6.5 |
| Active Pigment (Amine-Complexed Zinc Salt) | 36.7 |
| Letdown | |
| Natrosol 250HR (Hercules Incorporated) | 0.06 |
| Rhoplex MV23 (43%) (Rohm & Haas) | 193.7 |
| Texanol (Eastman Kodak) | 2.0 |
| Aroplaz 1271 (100%) (Spencer Kellog-Div. of Textron) | 21.4 |
| Zr Drier (Tenneco Chemicals Inc.) | 5 drops |
| Co Drier (Tenneco Chemicals Inc.) | 2 drops |
| Triton X100 (Rohm & Haas) | 1.5 |
| Ethylene Glycol (Union Carbide Corp.) | 9.3 |
| Colloid 681F (Colloids) | 0.88 |
| E-845 (Rohm & Haas) | 13.6 |
| NaNO$_2$ (13.8%)(Fisher Scientific) | 2.8 |

TABLE XI

| Alkyd Formulation | |
|---|---|
| Reactants | Grams |
| Alkyd Resin-Varkyd 1S31-50E (McCloskey Varnish Co.) | 183 |
| Active Pigment | 34 |
| Titanox 2160 (NL Industries) | 25.4 |
| Emtal 500 (Engelhard Corporation) | 56.8 |
| Bentone 38 (NL Industries) | 1.7 |
| Mineral Spirits | 36.5 |
| Zr Drier (18%) (Tenneco Chemicals Inc.) | 1.1 |
| Co Drier (12%) (Tenneco Chemicals Inc.) | 0.52 |
| Exkin (Tenneco Chemicals Inc.) | 0.34 |

Figure 2:
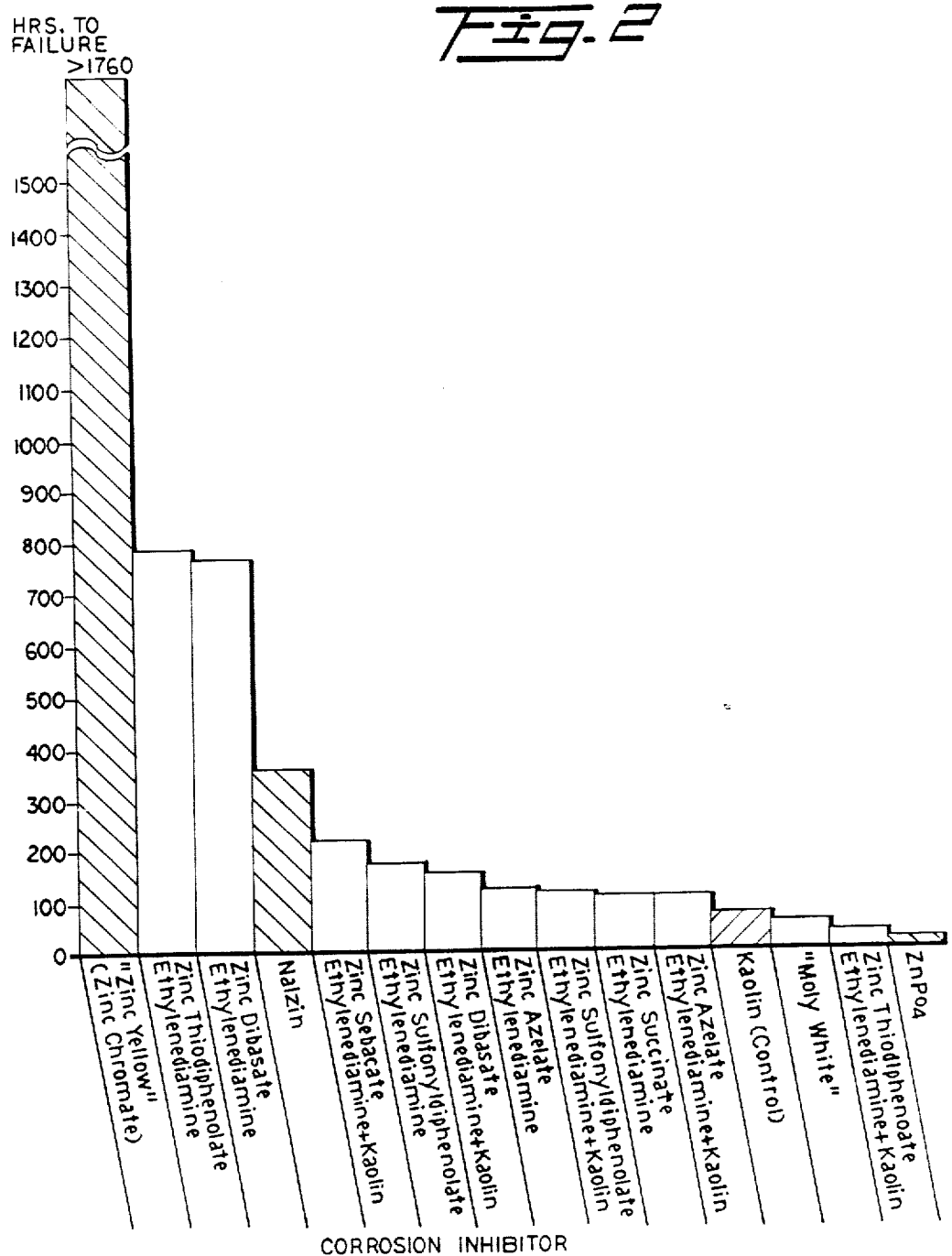
FIGS. 2 and 4 are similar graphs for latex formulations containing various corrosion inhibitors.

In each instance the primers were applied on low carbon steel panels in a single coat of about 2.5-3.5 mils dry film thickness. After ambient air-curing for two weeks the panels were exposed to salt spray exposure in accordance with the procedure of ASTM D-117-73. The test results are shown in FIGS. 1 and 2. FIG. 1 is a bar graph of the performance, denoted as hours to failure, for various corrosion inhibitor-containing alkyd formulations. As seen from this bar graph, the commercial "Zinc Yellow" (zinc chromate) formulation gave high performance, with a performance life of about 1050 hours in the salt spray exposure. Nonetheless, as previously indicated, the zinc chromate pigment in this composition is highly toxic in character. In contrast, various corrosion-inhibitor compounds and composites of the invention, characterized by significantly lower toxicity levels, performed on a comparable level to this commercial corrosion inhibitor pigment. For example, the composite pigments based on zinc sebacate ethylenediamine and zinc sulfonyldiphenolate ethylenediamine in combination with kaolin gave performance life values of approximately 1,000 hours and 850 hours, respectively. By contrast, the performance of commercial pigments such as zinc phosphate and Nalzin SC-1 (NL Industries) were markedly inferior in performance to the corrosion-inhibitor compounds and composites of the present invention. It is to be noted that the formulation containing only kaolin (control) had a performance life of approximately 750 hours, and this high performance life believed due to the presence of a dispersant, TSPP, present in the kaolin for the purpose of rendering the same water-dispersible.

As mentioned above, the longest-performing corrosion inhibitors of the present invention were distended on kaolin, and kaolin likewise enhanced the performance of zinc thiodiphenolate ethylenediamine, but anomolously reduced the performance of zinc azelate ethylenediamine.

FIG. 2 is a similar bar graph showing salt spray exposure performance for panels coated with latex formulations with various corrosion-inhibitor additives. The data show that in latex formulations, the amine-complexed zinc salts of the present invention are not characterized by long performance life such as is the commercially available "Zinc Yellow" (zinc chromate) pigment, however zinc thiodiphenolate ethylenediamine and zinc dibasate ethylenediamine provided performance levels of approximately 780 hours and 760 hours, respectively. In addition, virtually all of the corrosion inhibitor compounds and composites of the invention which were tested for the FIG. 2 comparison exhibited better performance than the commercial pigments, "Moly White" and zinc phosphate.

EXAMPLE VI

In this test, as in Example V, various illustrative corrosion-inhibitor compounds and composites were tested against various commercial corrosion-inhibitor pigments in salt spray exposure in accordance with the procedure of ASTM B117-73.

The panels used in all exposure testing were Q-panels SAE 1010 cold rolled steel, 3 inches by 6 inches by 0.032 inch, polished on one side in accordance with the specification (Type 2) set forth in ASTM D-609. The polished face of the test panel was solvent-wiped with a 50:50 mixture of xylene and VM&P naphtha according to the procedures set out in ASTM D-609, method D.

One coat of paint was applied using a Henry K. Gardner Laboratory draw-down, with either a 6 mil or 8 mil draw-down blade. The draw-down speed was 1 inch per second. Such coat of paint was allowed to cure for two weeks under ambient conditions, in the case of both alkyd and latex paints. The dried coating thickness was measured with Elcometer Coating thickness gauge, Model #150/-FNIE. Acceptable thickness of the cured film were 2.5–3.5 mils.

The alkyd and latex formulations employed in these tests are set out in Tables XII and XIII, respectively. Stormer viscosity (ASTM D562-55) for all alkyd paints was greater than 90, and for all latex paints was greater than 80.

TABLE XII

Alkyd Primer Formulation

| Reactants | lbs. | gals. |
|---|---|---|
| Varkyd 1531-50E[a](McCloskey Varnish Co.) | 505.0 | 66.4 |
| Emtal 500 (Engelhard Corporation) | 164.3 | 7.1 |
| Titanox 2160 (NL Industries) | 70.0 | 2.1 |
| Active Pigment | 93.9 | 7.7 |
| Bentone 38 (NL Industries) | 4.7 | 0.29 |
| Exkin (Tenneco Chemicals Inc.) | 0.94 | 0.12 |
| Mineral Spirits | 100.8 | 15.8 |
| Zr Drier 18% (Tenneco Chemicals Inc.) | 3.1 | 0.33 |
| Co Drier 12% (Tenneco Chemicals Inc.) | 1.5 | 0.17 |
| | 944.2 | 100.0 |

NVV (non-volatile content of paint, by volume) = 45%
PVC (pigment content in dried film, by volume) = 38%
[a]Medium oil, soya linseed

TABLE XIII

Latex Primer Formulation

| | lbs. | gals. |
|---|---|---|
| Grind | | |
| Water | 117.9 | 14.1 |
| Nopco NDW (Nopco Chemical) | 2.7 | 0.36 |
| NH₄OH (28%)(Carco Chemicals Corps.) | 6.8 | 0.90 |
| Tamol 850 (Rohm & Haas) | 9.8 | 0.99 |
| Triton CF-10 (Rohm & Haas) | 5.1 | 0.51 |
| TSPP (Alfa Products-Thiokol) | 4.9 | 0.32 |
| Chemcarb 11 (Engelhard Corporation) | 38.2 | 1.69 |
| Kadox 515 (New Jersey Zinc Co.) | 11.2 | 0.24 |
| Titanox 2160 (NL Industries) | 16.1 | 0.45 |
| Active Pigment | 92.9 | 7.62 |
| Natrasol 250HR (Hercules Inc.) | 0.15 | 0.0084 |
| Letdown | | |
| Rhoplex MV23 (Rohm & Haas) | 485.6 | 55.5 |
| Aroplax 1271 (Spencer Kellogg) | 53.7 | 6.44 |
| Zr Drier 18% (Tenneco Chemical Inc.) | 0.075 | 0.075 |
| Co Drier 12% (Tenneco Chemical Inc.) | 0.030 | 0.030 |
| Triton X100 (Rohm & Haas) | 4.1 | 0.45 |
| Glycol (Union Carbide Corp.) | 35.1 | 3.76 |
| Foamaster VL (Nopco Chemical) | 4.2 | 0.45 |
| Texanol (Eastman Chemicals) | 5.8 | 0.75 |
| E845 (Rohm & Haas) | 39.5 | 4.55 |
| NaNO₂(13.8%) (Fisher Scientific) | 7.2 | 0.78 |
| | 941.1 | 100.0 |

NVV (non-volatile content of paint, by volume) = 38%
PVC (pigment content in dried film, by volume) = 26%

Figure 3:
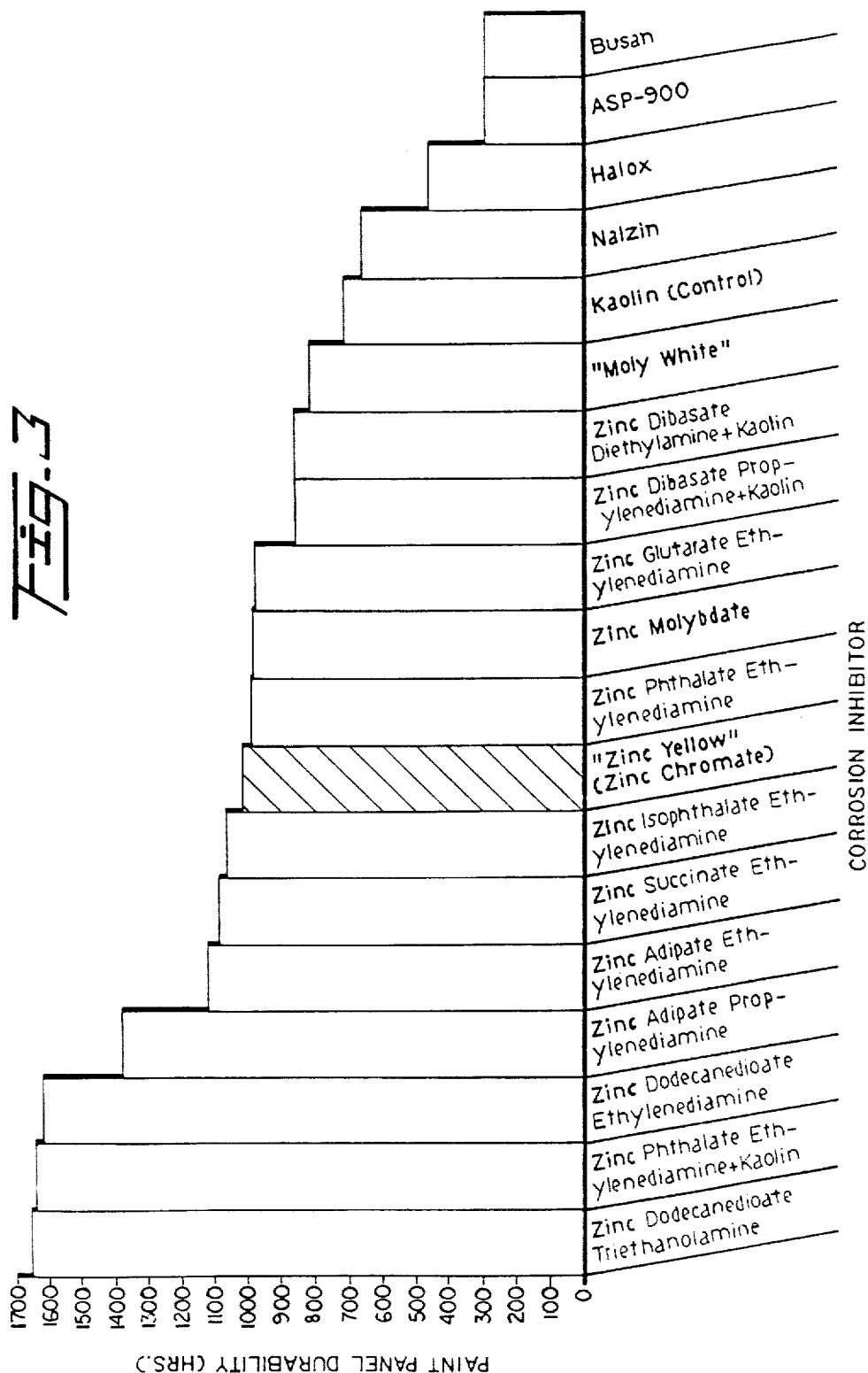

The results for alkyd formulation testing are set forth in FIG. 3, which is a bar graph of the type shown in preceeding FIGS. 1 and 2. These data show that various corrosion-inhibitor compounds and composites of the invention were superior to "Zinc Yellow" (zinc chromate) in salt spray durability. These superior compounds and composites including zinc dodecanedioate triethanolamine (compound 10), zinc phthalate ethylene diamine (compound 17) in distended form on kaolin, zinc dodecanedioate ethylenediamine (compound 11), zinc adipate propylenediamine (compound 4), zinc adipate ethylenediamine (compound 3), zinc succinate ethylenediamine (compound 1), and zinc isophthalate ethylenediamine (compound 18). The remaining compounds and composite corrosion inhibitors of the invention, as shown, generally performed along the lines of the "Zinc Yellow" and "Moly White" commercially available pigments. Further, all compounds and composite corrosion inhibitors of the invention were significantly better in performance than commercial corrosion inhibitor additives such as Nalzin, Halox and Busan. Also shown in FIG. 3 for the purpose of comparison are salt spray durability performances of zinc molybdate-containing formulations and formulations containing ASP-900, another commercially available mineral filler (Engelhard Corporation, Menlo Park, N.J.).

Figure 4:
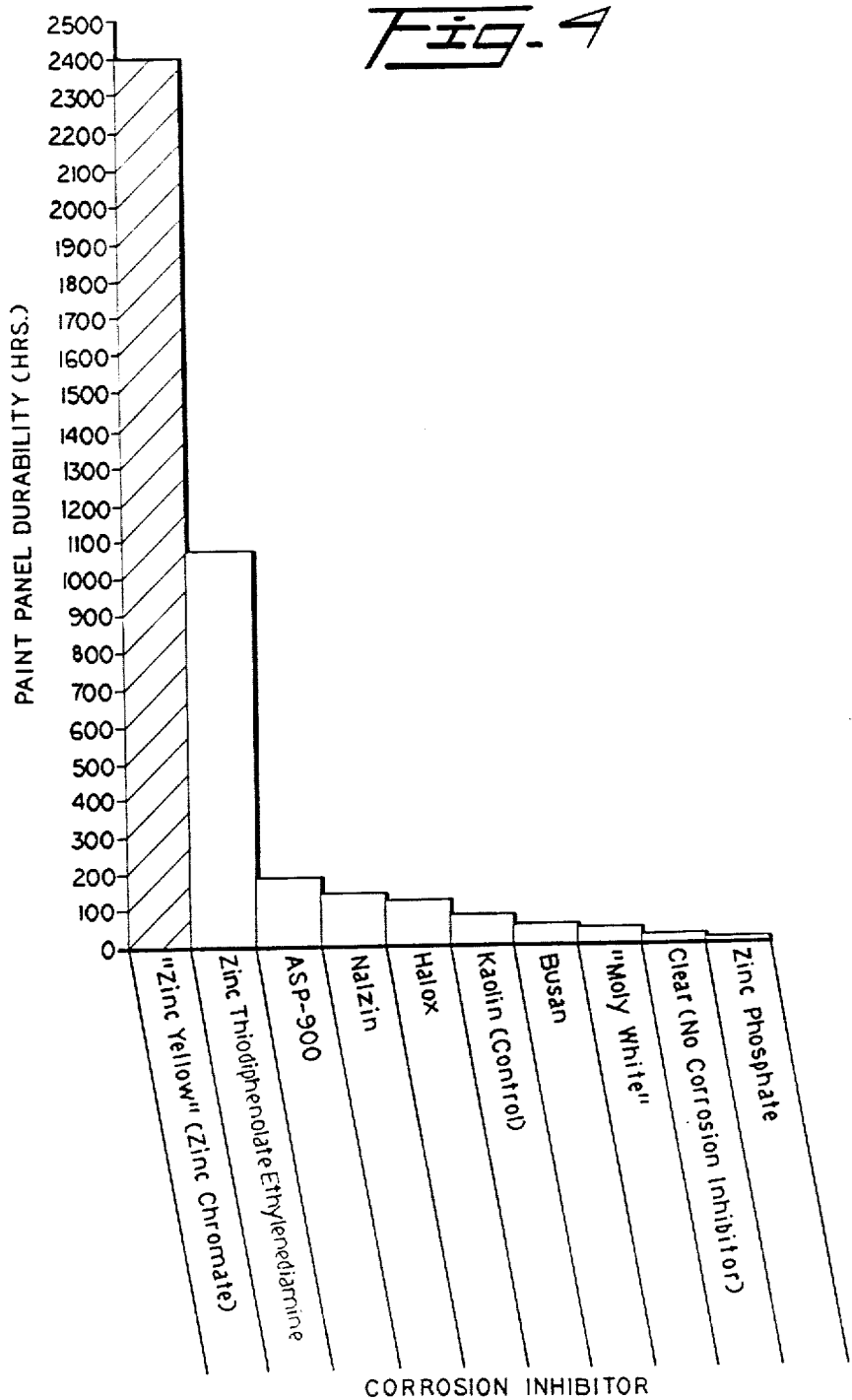

FIG. 4 is a bar graph similar in format to FIGS. 1–3, wherein paint panel durability, in hours (to failure) is indicated for various corrosion inhibitors in latex vehicle formulations. This plot shows that the zinc thiodiphenolate ethylenediamine of the present invention gave slightly less than half the durability achieved by the commercial "Zinc Yellow" (zinc chromate) corrosion-inhibitor formulation. Nonetheless, such amine-complexed zinc salt performed markedly better than commercially available corrosion inhibitors, such as Nalzin, Halox, Busan, "Moly White" and zinc phosphate.

EXAMPLE VII

In a test of the efficacy of selected compounds of the invention for use as marine-fouling inhibiting pigments, compounds 6 and 14 of Table II (zinc sebacate ethylenediamine and zinc thiodiphenolate ethylenediamine, respectively) were prepared and formulated into alkyd paints. The compounds were prepared by reacting ZnO, ethylenediamine and, respectively, 4,4'-thiodiphenol and sebacic acid, as follows.

The amounts of reactants utilized were as follows:

| Reagents | Amount (grams) | |
|---|---|---|
| | Compound 6 | Compound 14 |
| Zno (Reagent grade) | 117.5 | 90.4 |
| 4,4'-thiodiphenol (Crown Zellerbach) | — | 242.0 |
| Sebacic acid (Reagent grade) | 294.5 | — |
| Ethylenediamine (Reagent grade) | 88.5 | 68.0 |

Each reaction was carried out with constant agitation of the reaction batch. In each case, 3 liters of H₂O were added to a 4 liter breaker, the ZnO powder was mixed in and then ethylenediamine was added. Over a period of 10 minutes the remaining reactant, 4,4'-thiodiphenol or sebacic acid, was slowly added, the mixture was heated to 95°±5° C. and held at that temperature for one hour then cooled under agitation. The batch was allowed to sit overnight without agitation and then was filtered and the recovered solids were washed with 1.5 liters H₂O on a vacuum filter, were dried at 37.7° C. for 1-2 hours, and then pulverized. Three alkyd paint formulations were then prepared in a conventional manner, including being milled overnight with porcelain balls in a 1-pint mill, except that two of the paints were made up with about 95.9 grams per liter each (0.8 lbs per U.S. gallon) of, respectively, the sebacic acid-derived pigment and the thiodiphenol-derived pigment. The paint formulated with the sebacic acid-derived pigment is below identified as Formulation 6 and the paint formulated with the thiodiphenolate-derived pigment, as Formulation 14. A third, control paint formulation contains mica but no pigment and is identified as Formulation MC.

TABLE XIV

| Test Paint Formulations (Parts By Weight) | | | |
|---|---|---|---|
| | Formulations | | |
| Ingredient | MC | 6 | 14 |
| Varkyd 1531-50E (McCloskey) | 183.0 | 183.0 | 183.0 |
| Titanox 2160 (NL Industries) | 10.0 | 10.0 | 10.0 |
| 325 Mesh Waterground Mica (English Mica Co.) | 40.0 | 12 | 12 |
| Pigment | none | 28 | 28 |
| Emtal-500 | 95.8 | 63.4 | 63.3 |
| Exkin (Tenneco Chem. Inc.) | 0.34 | 0.34 | 0.34 |
| Mineral Spirits | 36.5 | 36.5 | 36.5 |
| Zr Drier (18%) | 1.1 | 1.1 | 1.1 |
| Co Drier (12%) | 0.52 | 0.52 | 0.52 |

The three test paint formulations were each applied to three aluminum test panels in a single coat on both sides and were immersed just below the water surface in brackish water (Cedarcroft Lagoon, Matedeconk River, Brick Town, N.J.) for a period of about two months, from August 1 to October 3. Results of visual observation of the test panels are shown in Table XV following.

TABLE XV

| Marine Fouling Test Results | | | | |
|---|---|---|---|---|
| | | Result | | |
| Paint Formulations | Panel Number | No. of Barnacles | Algae | Comments |
| MC | 1 | 17 | Yes | 2nd worst panel |
| MC | 2 | 1 | Yes | |
| MC | 3 | 16 | Yes | Worst panel |
| 6 | 1 | 12 | Yes | 3rd worst panel |
| 6 | 2 | 1 | Yes | |
| 6 | 3 | none | Yes | |
| 14 | 1 | none | Almost Clean | Best panel |
| 14 | 2 | none | Some | 2nd best panel |
| 14 | 3 | none | Yes | |

Although the invention has been described in detail with respect to certain preferred compounds, composites and embodiments, it will be appreciated by those skilled in the art that other compounds, composites and embodiments which may be usefully employed, lie within the scope of the present invention and the appended claims.

What is claimed is:

1. An amine-complexed zinc salt of an organic diacid selected from the group consisting of unchlorinated thiodiphenols, unchlorinated sulfonyldiphenols, and phthalic acids, said salt being obtained as the reaction product of zinc oxide, said amine and said organic diacid in an approximately 1:1:1 molar ratio and having the formula $$ZnA_x \cdot B_y$$

wherein A is the organic diacid residue, B is the amine, x is between 0.6 and 1.0, y is between 0.03 and 0.87, and said amine is selected from the group consisting of alkylenediamines, C₂ to C₃ polyalkylamines and polyalkanol amines.

2. An amine-complexed zinc salt of an organic diacid selected from the group consisting of unhalogenated thiodiphenols, unhalogentated sulfonyldiphenols, and phthalic acids, said salt being obtained as the reaction product of zinc oxide, said amine and said organic diacid in an approximately 1:1:1 molar ratio and having the formula $$ZnA_x \cdot B_y$$

wherein A is the organic diacid residue, B is the amine, x is between 0.6 and 1.0, y is between 0.03 and 0.87, and said amine is selected from the group consisting of alkylenediamines, C₂ to C₃ polyalkylamines and polyalkanol amines.

3. An amine-complexed zinc salt of an organic diacid selected from the group consisting of thiodiphenols and sulfonyldiphenols and having the formula:

$$ZnA_x \cdot B_y$$

wherein A is the organic diacid residue, B is the amine, x is between 0.6 and 1.0 and y is between 0.01 and 1.0.

4. An amine-complexed zinc salt according to claim 3 wherein said organic diacid is selected from the group consisting of unhalogenated thiodiphenols and unhalogenated sulfonyldiphenols.

5. An amine-complexed zinc salt according to claim 3 or claim 4 wherein said amine is selected from the group consisting of alkylenediamines, polyalkylamines and polyalkanolamines.

6. An amine-complexed zinc salt according to claim 1, claim 2, claim 3 or claim 4 wherein said amine is selected from the group consisting of ethylenediamine and propylenediamine.

7. An amine-complexed zinc salt according to claim 1, claim 2 or claim 3 wherein said organic diacid is 4,4'-thiodiphenol.

8. An amine-complexed zinc salt according to claim 1, claim 2 or claim 3 wherein said organic diacid is 4,4'-sulfonyldiphenol.

9. An amine-complexed zinc salt according to claim 1, claim 2 or claim 3 wherein said organic diacid is selected from the group consisting of phthalic acid, isophthalic acid and terephthalic acid.

10. An amine-complexed zinc salt according to claim 3 formed as a reaction product of zinc oxide, said amine and said organic diacid.

11. An amine-complexed zinc salt according to claim 1, claim 2 or claim 3 wherein said amine is $C_2$–$C_3$ alkylenediamine.

12. An amine-complexed zinc salt according to claim 10 wherein the reaction product is obtained by reaction of said zinc oxide, said amine and said organic diacid in an approximately 1:1:1 molar ratio.

13. An amine-complexed zinc salt according to claim 1, claim 2 or claim 3 wherein the molar ratio of said organic diacid to said amine in the reaction is from about 1.0 to about 1.2.

14. An amine-complexed zinc salt according to claim 2 or claim 3 wherein said amine is a $C_2$–$C_3$ alkylene diamine of an organic diacid selected from the group consisting of unhalogenated thiodiphenol and unhalogenated sulfonyldiphenol.

15. An amine-complexed zinc salt according to claim 1, claim 2 or claim 3 wherein said amine is ethylene diamine and said organic diacid is selected from the group consisting of phthalic acid, isophthalic acid and terephthalic acid.

16. An amine-complexed zinc salt according to claim 3 wherein y is between 0.03 and 0.87.

17. An amine-complexed zinc salt formed as the reaction product of zinc oxide, said amine and an organic diacid selected from the group consisting of thiodiphenols and sulfonyldiphenols, wherein said reaction product is obtained by reaction of said zinc oxide, said amine and said organic diacid in an approximately 1:1:1 molar ratio.

* * * * *